United States Patent [19]

Truett

[11] Patent Number: 5,905,144
[45] Date of Patent: May 18, 1999

[54] ANTIVIRALS AND PROCESS FOR PREPARATION

[75] Inventor: William L. Truett, 42 Wolf Rd. Apt. 321, Lebanon, N.H. 03766

[73] Assignee: William L. Truett, Lebanon, N.H.

[21] Appl. No.: 08/929,475

[22] Filed: Sep. 15, 1997

Related U.S. Application Data

[63] Continuation of application No. 08/420,302, Apr. 11, 1995, Pat. No. 5,693,791.

[51] Int. Cl.$^6$ .................................................. A61K 31/70
[52] U.S. Cl. ..................... 536/22.1; 536/23.1; 536/27.1; 536/28.1
[58] Field of Search .................................. 536/22.1, 23.1, 536/27.1, 28.1

[56] References Cited

U.S. PATENT DOCUMENTS

| | | | |
|---|---|---|---|
| 4,837,311 | 6/1989 | Tam et al. | 536/22 |
| 5,214,134 | 5/1993 | Weis | 536/253 |
| 5,221,693 | 6/1993 | Shetty | 514/635 |
| 5,393,883 | 2/1995 | Blumenhopf | 544/124 |
| 5,585,364 | 12/1996 | Walker | 514/47 |
| 5,594,110 | 1/1997 | Fiume | 530/362 |
| 5,693,791 | 12/1997 | Truett | 540/222 |

*Primary Examiner*—Mukund J. Shah
*Assistant Examiner*—Pavanaram K. Sripada
*Attorney, Agent, or Firm*—Herbert M. Wolfson

[57] ABSTRACT

A series of novel antivirals are disclosed intended to attack a broad range of DNA and RNA viruses, in which nucleosides closely related entities are linked via reaction with a diacid chloride of the general structure $COCl-(CH_2)_n-COCl$ wherein n is two or greater.

4 Claims, No Drawings

ANTIVIRALS AND PROCESS FOR PREPARATION

This is a continuation of application Ser. No. 08/420302, filed Apr. 11, 1995.

BACKGROUND THE INVENTION

This invention relates to novel antiviral compounds and compositions for the treatment of human viral infections. The compounds contain various combinations of nucleoside moities and various combinations of purine moities and other heterocyclic structures shown to possess antiviral activity.

The mechanism of the interference with viral reproduction in the host is varied and may be any of the following: block virus attachment to cells, block uncoating of the virus, inhibit vivid protein synthesis, inhibit specific virus enzyme, inhibit virus assembly, inhibit virus release, or simply stimulate the host immune system. There are several organic structural classes of antiviral at present: such as aminoamatadines which apparently block attachment of the virus to the cell wall of the host; a wide variety of nucleoside structures, which is a combination of a DNA or RNA base, together with a six-carbon sugar, which unlinks DNA polymerase; pyrimidines with various attached moieties which also inhibit DNA polymerase.

All of these antiviral compounds have several limitations. In general the range of viruses killed or inhibited is quite narrow, commonly a single type such as influenza type A. Also, surprisingly, resistance tends to arise rapidly in the virus, requiring an endless quest for new antivirals. Alternately, as in HIV therapy, complex combinations of agents are utilized consisting of giving three or more specific drugs in a complex regime of dosage requiring constant monitoring to be sure of effectiveness. This is difficult for the patient to comply with, what with the complex pattern of when and what medication to ingest, and it is even a puzzle to physicians at times. Also, resistance develops to the medications in many patients due to the ease of genetic change by the HIV entity.

It has now been found that an alternative to the above problems of the need for a broad-spectrum antiviral drug and a drug resistant to viral genetics can be realized via chemical combinations of known effective antiviral compounds. A single example is to link two or more anti-HIV drugs by means of reaction with a linking agents such as a diacid chloride, or the like. This can be extended to the many examples developed below. The synergistic effects can be remarkable when the virus is contacted simultaneously with attacks from several quarters at the key stages of its complex life cycle in the human host cell.

SUMMARY OF THE INVENTION

The concept of linking two antiviral agents has been extended to three groups of compounds, linked by succinic acid chloride.

The first group comprises the linking of two groups of nucleosides with Ribavirin and Vidarabine. The nucleosides linked with the hydroxy containing broad spectrum Ribavirin are:
3'-azido-2',3'-dideoxy thymidine
2',3'-didehydrothymidine
3'-deoxy-2',3'-didehydrothymidine
and
Ribavirin, 1-Beta-D-Ribofranosyl-1H-1,2,4-triazole-3-carboxamide
to form a group of diesters.

The nucleosides with amino containing groups that are linked with Vidarabine, 9-Beta-D-Arabinofuranosyl-9H-purine-6-amine, are:
2'-3'-dideoxycytidine, and (2R,cis)-4-amino-1,(2-hydroxymethyl-1,3-oxathiolan-5-yl)-(1H)-pyrimidin-2-one
to form a group of diamides.

The primary target virus of this first group is HIV.

The second group comprises substituted purines inked to Vidarabine-9-Beta-D-Arabinofuranosyl-9H- purine-6-amine:
2-amino-1,9-dihydro-9-[12-hydroxy-ethoxymethyl]-6H-purine-6-one;
2-amino-1,9[[2-hydroxy-1-(hydroxymethyl)ethoxy]methyl]-6H-purin-6-one;
and
2-[2-(2-amino-9H-purin-9-yl)ethyl]1,3-propanediol diacetate,
forming a group of diamides.

The primary target of the second group is the herpes simplex virus.

The third group comprises the inking of Vidarabine-9-Beta-D-Arabinofuranosyl-9H-purin-6-amine and Ribavirin-1-Beta-D-Ribofuranosyl-1H-,1,2,4-triazole-3-carboxamide to form an amide ester.

The primary target of this compound is broadly virtually all RNA and DNA viruses.

DETAILED DESCRIPTION OF THE INVENTION

The concept of linking two antiviral agent via reaction with a diacid chloride of the general formula COCl$(CH_2)_n$—COCl in which n is 2 or more has been extended to three groups of compounds.

The first set of compounds comprises linking two sets of nucleosides with Ribavirin (1-Beta-Ribofuranosyl-1H-1,2,4-triazole-3-carboxamide) and Vidarabine (9-Beta-D-Arabinofuranosyl-9H-purine-6-amine).

The group linked wit Ribavirin from a series of diesters, since all the structures contain a preferentially reactive primary hydroxyl group. The structures are as follows:

1. Ribavirin-1-Beta-D-Ribofuranosyl-1H-1,2,4-triazole-3-carboxamide

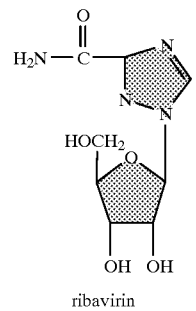

ribavirin 2. 3'-azido-2',3'-dideoxythymidine

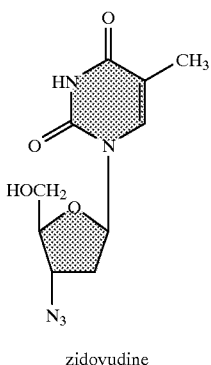

zidovudine 3. 2',3'-dideoxyinosine

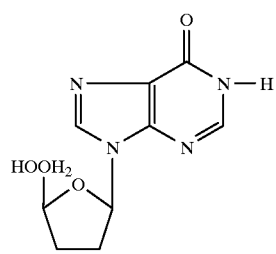

4. 3'-dioxy-2',3'-didehydrothymidine

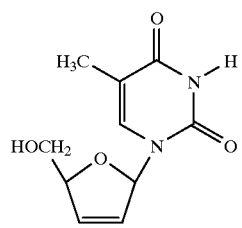

The general formula for this group of diesters formed from the condensation of the several nucleosides and succinic acid dichloride is:

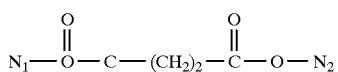

in which $N_1$ is structure 1 and $N_2$ is drawn from the group of structures 2,3 and 4.

The structure formed from the reaction of 1 and 2 with succinic acid and dichloride is

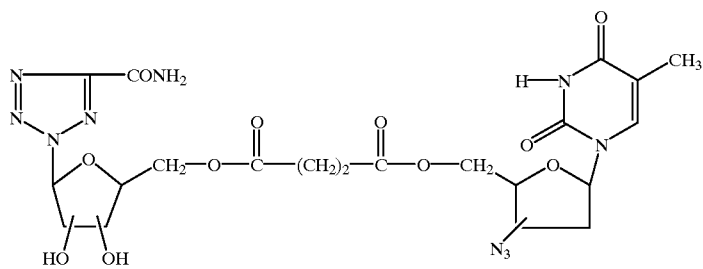

The reaction of 1 and 3, and 1 and 4 yield analogous structures.

Method A—see Experiment—is utilized to form the desired diester products.

The second group of compounds comprises a purine with a set of nucleosides.

The group linked with Vidarabine from a series of diamides, since all structures contain a preferentially reactive amino group. The structures are as follows:

5. Vidarabine(9-Beta-D-Arabinofuranosyl-9H-purine-6-amine).

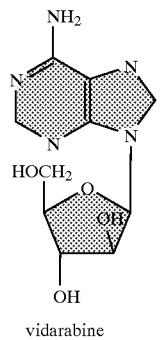

vidarabine 6. (−)2',3'-dideoxy-3'-thiacytidine

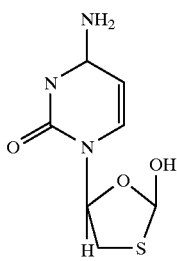

7. 2',3'-dideoxycytidine

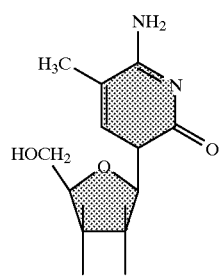

The general formula for this group of diamides formed from the condensation of the several nucleosides and succinic acid chloride is

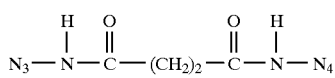

in which N₃ is structure 5 and N₄ is structures 6 or 7.

The structural formula from the reaction of 5 and 6 is

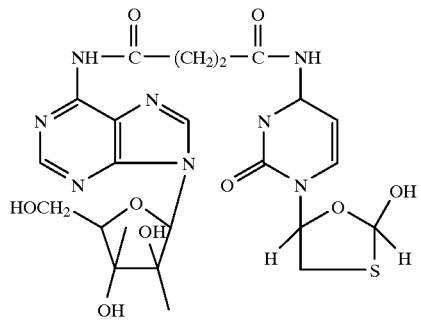

The reaction of 5 and 7 will yield an analogous structure.

Method B—see Experimental—is utilized to form the desired diamide products.

The target virus for the above diesters and diamides is HIV.

The second set of compounds comprises linking a set of substituted purines to Vidarabine -5. 9-Beta-D-Arabinofuranosyl-9H-purine-6-amine.

8. 2-amino-1,9-dihydro-9-[(2-hydroxy-ethoxy)methyl]-6H-purin-6-one.

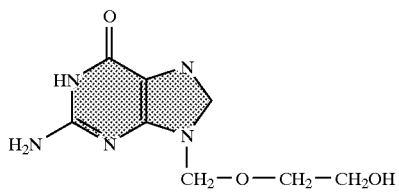

acyclovir 9. 2-amino-1,9[[(2-hydroxy-1-hydroxymethyl)ethoxy]methyl]methyl]-6-H-purin-6-one.

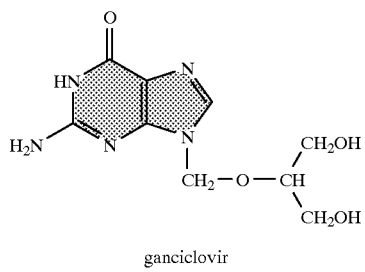

ganciclovir 10. 2-[2-(2-amino-9H-purin-9-yl)ethyl]-1,3propane diol diacetate.

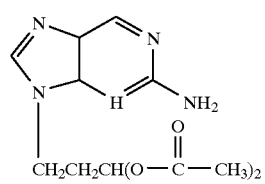

The general formula for this set of diamides formed from the condensation of several substituted purines and the nucleoside with succinic acid dichloride is

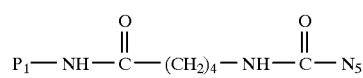

in which $P_1$ is one of three purines $N_5$ is the nucleoside.

The structural formula for the condensation of 5 and 8 with succinic acid dichloride is:

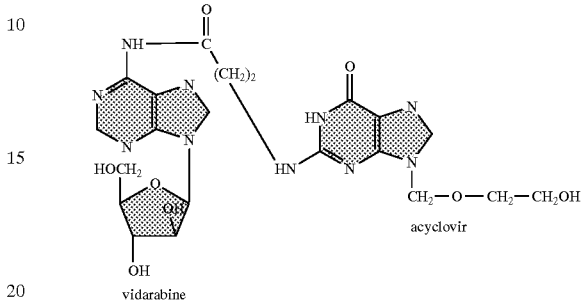

The reaction of 5-9 and 5-10 follows an analogous path.

Method B, see Experimental, is utilized to form the diamide products.

The target virus for these diamides is herpes simplex and related herpes viruses.

The third group comprises linking Vidarabine- 9-Beta-D-Arabino-furanosyl-9H-purine-6-amine with Ribavarin-1-Beta-D-Ribofuranosyl-1H-1,2,4-triazole-3-carboxamide- with succinic acid chloride to form an ester amide as shown below:

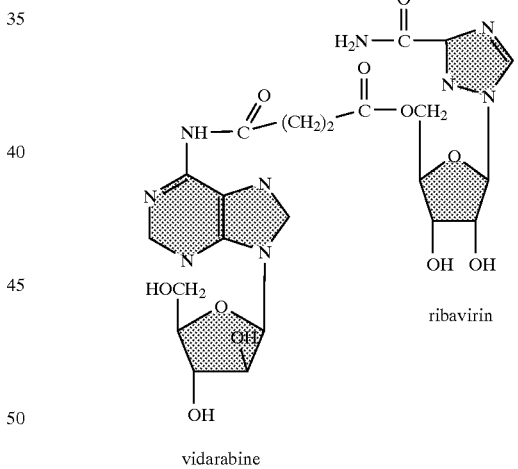

Method C—see Experimental—is utilized to form this ester amide, first creating the amide linkage, followed by the ester linkage, the amine reaction more rapidly than the primary ester group in structure 1.

This structure—the ester amide is designed to comprise a broad spectrum antiviral capable of suppressing a wide variety of DNA and RNA viruses in human and animals infections.

EXPERIMENTAL

Methods of linking nucleosides by means of succinyl acid dichloride:

| Method A—Formation of Diesters | |
|---|---|
| Solvents: | 50 ml anhydrous pyridine |
| Temperature: | 0–50° C. |
| Time: | 5–10 hours |
| Quantities: | 0.01 mole each nucleoside |
| | 0.005 mole succinic acid dichloride |
| Monitor Reaction | Via IR spectroscopy |
| Reaction Vessel | 100 ml RB 3 neck flask, equipped with stirrer, thermometer, heater and addition port |
| Work Up | When IR spectroscopy indicates all acid chloride has been consumed an excess of bicarbonate is added to consume all HCl. The product is precipitated with water and fractionated via flash chromatography, products being characterized by IR spectroscopy for identification. |

Preminimary in vitro investigation of antiviral activity is performed.

Precisely analogous to Method A.

Method B—Formation of Diamide

Precisely analogous to Method A.

Method C—Formation of Ester Amide

The reaction was performed analogously to A and B with the exception that the —OH group containing entity, Ribavirin, was added initially, and when IR spectroscopy indicates the acid chloride is one-half consumed the Vidarabine is added and the reaction continued until all acid chloride is consumed.

What is claimed is:

1. A process for preparing anti-HIV pharmaceutical comprising reacting two nucleoside compounds selected from the group consisting of
1-Beta-D-Ribofuranosyl-1H-1,2,4-triazole-3-carboxamide;
3'-azido-2,3'-dideoxythymidine;
2,'3'-dideoxyinosine; and
3'-dioxy-2',3'-dihydrothymidine
in the presence of a diacid chloride having the formula $COCl(CH_2)_nCOCl$ where "n" is an integer equal to at least 2,
to form a diester through linkage of the primary hydroxyl group of said two nucleoside compounds to each of the COCl group of said diacid chloride; and isolating said diester.

2. A process for preparing anti-HIV pharmaceuticals comprising reacting two nucleoside compounds
(−)2',2'-dideoxy-3'-thiacytidine
with
2',3'-dideoxycytidine
in the presence of a diacid chloride having the formula $COCl(CH_2)_nCOCl$ where "n" is an integer equal to at least 2,
to form a diamide through linkage of the reactive amine of said compounds with each of the COCl groups of said diacid chloride; and isolating said diamide.

3. A process for preparing an anti-herpes viral compound comprising reacting at least one substituted purine selected from the group consisting of
2-amino-1,9-dihydro-9-[(2-hydroxy-ethoxy)methyl]-6H-purin-6-one;
2-amino-1,9{[(2-hydroxy-1-hydroxymethyl)ethoxy]methyl}-6-purin-6-one; and
2[2-(2-amino-9H-purin-9-yl)ethyyl]-1,3-propane diol diacetate with the nucleoside
9-Beta-D-Arabinofuranosyl-9H-purine-6-amine, in the presence of a diacid chloride of the general formula $COCl(CH_2)_nCOCl$ where "n" is an integer equal to at least 2,
to form a diamide; and isolating said diamide.

4. A process for preparing an anti-viral pharamceutical compound by racting Vidarabine (9-Beta-D-Arabnofuranozyl-9H-purine-6-amine) with Ribavirin (1-Beta-D-Ribofuranosyl-1H-1,2,4-triazole-3-carboxamide), in the presence of a diacid chloride of the general formula $COCl(CH_2)_nCOCl$ wherein "n" is an interger equal to at least 2,
to form an ester amide of the structure

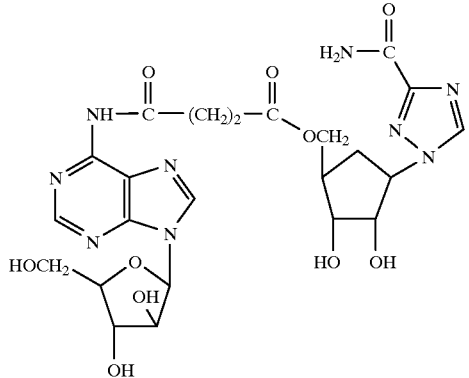

an isolating said ester amide.

* * * * *